United States Patent
Frayling

(10) Patent No.: US 10,000,794 B2
(45) Date of Patent: Jun. 19, 2018

(54) DROPLET STORAGE METHOD

(71) Applicant: BASE4 INNOVATION LTD, Cambridge, Cambridgeshire (GB)

(72) Inventor: Cameron Alexander Frayling, Cambridge (GB)

(73) Assignee: BASE4 INNOVATION LTD, Cambridge (GB)

( * ) Notice: Subject to any disclaimer, the term of this patent is extended or adjusted under 35 U.S.C. 154(b) by 423 days.

(21) Appl. No.: 14/897,069

(22) PCT Filed: Jun. 13, 2014

(86) PCT No.: PCT/GB2014/000232
§ 371 (c)(1),
(2) Date: Dec. 9, 2015

(87) PCT Pub. No.: WO2014/199113
PCT Pub. Date: Dec. 18, 2014

(65) Prior Publication Data
US 2016/0122802 A1    May 5, 2016

(30) Foreign Application Priority Data

Jun. 13, 2013 (GB) .................................. 1310584.6

(51) Int. Cl.
| C12Q 1/68 | (2018.01) |
| B01L 3/02 | (2006.01) |
| B01L 3/00 | (2006.01) |

(52) U.S. Cl.
CPC .......... C12Q 1/6806 (2013.01); B01L 3/0241 (2013.01); B01L 3/502761 (2013.01);
(Continued)

(58) Field of Classification Search
None
See application file for complete search history.

(56) References Cited

U.S. PATENT DOCUMENTS

| 5,528,046 A | 6/1996 | Ishikawa |
| 5,674,743 A | 10/1997 | Ulmer |
| (Continued) | | |

FOREIGN PATENT DOCUMENTS

| EP | 1 933 138 | 6/2008 |
| JP | 6-148076 | 5/1994 |
| (Continued) | | |

OTHER PUBLICATIONS

Written Opinion of the International Searching Authority and International Search Report dated Oct. 1, 2014 in International (PCT) Application No. PCT/GB2014/000232.

(Continued)

*Primary Examiner* — Kaijiang Zhang
(74) *Attorney, Agent, or Firm* — Wenderoth, Lind & Ponack, L.L.P.

(57) ABSTRACT

A method of storing a stream of droplets at least some of which comprise one or more single nucleotides and/or oligonucleotides, and a droplet fluid is provided. It is characterized by the step of introducing each droplet sequentially onto a surface of a substrate at a corresponding unique location and further characterized in that the stream of droplets is prepared by a process which includes the steps of generating an ordered stream of nucleotides from the analyte by progressive pyrophosphorolysis or exo nucleolysis and capturing each nucleotide in a corresponding droplet. The method can advantageously be used in association with microdroplet droplet sequencers and an analysis unit in which the sequence of nucleotides in a precursor polynucleotide analyte is determined using fluorescence spectroscopy. A device for carrying out the method is also described.

26 Claims, 2 Drawing Sheets

Figure 1:
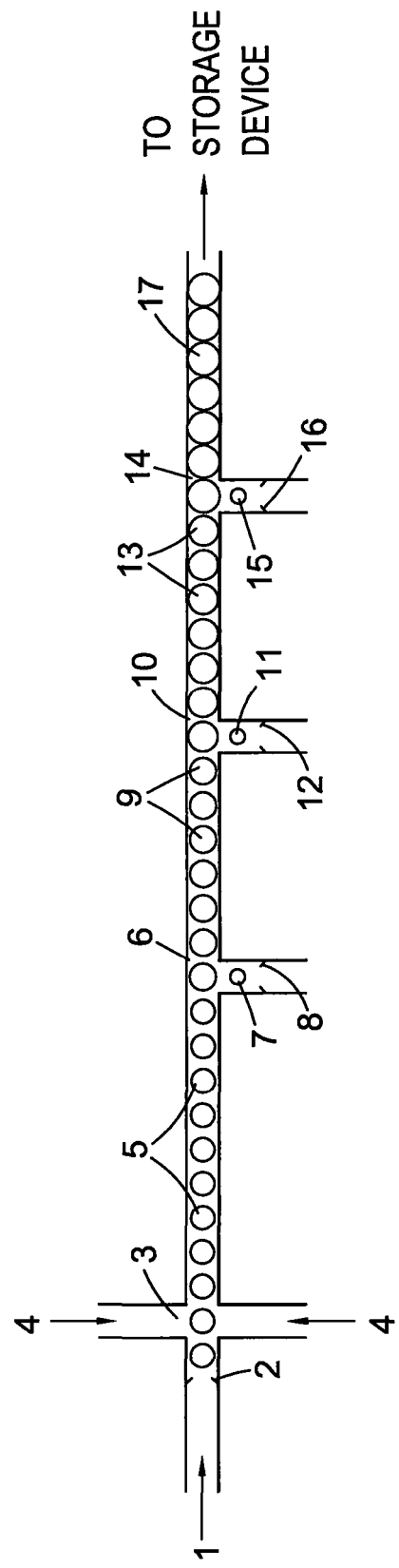

(52) U.S. Cl.
CPC .............. *B01L 3/52* (2013.01); *C12Q 1/6869* (2013.01); *B01L 2200/0605* (2013.01); *B01L 2200/0642* (2013.01); *B01L 2300/0864* (2013.01); *B01L 2300/0893* (2013.01)

(56) References Cited

U.S. PATENT DOCUMENTS

| | | |
|---|---|---|
| 6,277,334 B1 | 8/2001 | Ecker et al. |
| 2003/0138831 A1 | 7/2003 | Kwagh et al. |
| 2004/0197817 A1 | 10/2004 | Caren et al. |
| 2010/0015614 A1 | 1/2010 | Beer et al. |

FOREIGN PATENT DOCUMENTS

| | | |
|---|---|---|
| WO | 98/58240 | 12/1998 |
| WO | 03/080861 | 10/2003 |
| WO | 2005/049787 | 6/2005 |

OTHER PUBLICATIONS

Search Report dated Dec. 11, 2013 in corresponding Great Britain Application No. 1310584.6.

DROPLET STORAGE METHOD

The present invention relates to a method of storing droplets on the surface of a substrate. In particular, it relates to the storage of liquid droplets each of which contains one or more single nucleotides or oligonucleotides. The method is useful for the storage and characterisation of very large numbers of microdroplets such as may be generated in the sequencing of a polynucleotide analyte derived from naturally-occurring or synthetic DNA or RNA.

Next generation sequencing of genetic material is already making a significant impact on the biological sciences in general and medicine in particular as the unit cost of sequencing falls in line with the coming to market of faster and faster sequencing machines. Thus, in one such machine, a double-stranded DNA analyte is indirectly sequenced by first being broken down into a plurality of smaller polynucleotide fragments each of which is first adenylated on both ends of one strand so that a single-stranded first oligonucleotide can be bound to both ends of its compliment by hybridisation to the unpaired adenine base. The treated fragments so obtained are then size-selected and captured on a surface coated with bound single-stranded second oligonucleotides which themselves are the sequence compliment of the first so that in effect a library of surface-bound double-stranded fragments can be created by further hybridisation. In a subsequent clustering step, these library components are then clonally amplified millions of times on the surface using extension and isothermal bridging reactions to utilise unused second oligonucleotides. This, in effect, creates a dense concentration of the polynucleotide fragment bound to the surface through one of its strands. The unbound complimentary strand of each fragment is then removed to leave bound single-stranded fragments ready for sequencing. In the sequencing stage, each of these single-stranded fragments is primed and its complimentary strand recreated by extension using the polymerase chain reaction and a mixture of the four characteristic nucleotide bases of DNA in dideoxynucleotide triphosphate (ddNTP) form. Each ddNTP type is end-blocked with a moiety which is labelled with a different fluorophore fluorescing at a different wavelength. The extension reaction then takes the form of a cycle of three steps; first the relevant ddNTP is bound to the growing strand; secondly the nucleotide base it contains is identified by illuminating the sample and detecting the wavelength of the fluorescence and finally the end block and its associated fluorophore are removed to allow the next extension event to occur. By this means, the sequence of the complimentary strand can be built up base-by-base. It will be appreciated that, whilst this approach can be highly automated and can generate sequence reads of high accuracy, its speed of operation is limited by the rate of the extension cycle. Thus, in practice, use of the technology tends to involve parallel processing of relatively short polynucleotide fragments and assembly of the whole sequence from the various reads obtained therefrom. This in itself can lead to computational complexities and the potential introduction of errors.

More recently efforts have been made to develop alternative direct sequencing methods. For example, WO 2009/030953 discloses a new fast sequencer in which inter alia the sequence of nucleotide bases or base pairs in a single- or double-stranded polynucleotide sample (e.g. naturally occurring RNA or DNA) is read by translocating the same through a nano-perforated substrate provided with plasmonic nanostructures juxtaposed within or adjacent the outlet of the nanopores. In this device, the plasmonic nanostructures define detection windows (essentially an electromagnetic field) within which each nucleotide base (optionally labelled) is in turn induced to fluoresce or Raman-scatter photons in a characteristic way by interaction with incident light. The photons so generated are then detected remotely, multiplexed and converted into a data stream whose information content is characteristic of the nucleotide base sequence associated with the polynucleotide. This sequence can then be recovered from the data stream using computational algorithms embodied in corresponding software programmed into a microprocessor integral therewith or in an ancillary computing device attached thereto. Further background on the use of plasmonic nanostructures and their associated resonance characteristics can be found in for example Adv. Mat. 2004, 16(19) pp. 1685-1706.

Another apparatus for fast sequencing polynucleotides is described, for example, in U.S. Pat. No. 6,627,067, U.S. Pat. No. 6,267,872 and U.S. Pat. No. 6,746,594. In its simplest form, this device employs electrodes, instead of plasmonic nanostructures, to define the detection window across the substrate or in or around the outlet of the nanopore. A potential difference is then applied across the electrodes and changes in the electrical characteristics of the ionic medium flowing therebetween, as a consequence of the electrophoretic translocation of the polynucleotide and associated electrolyte through the nanopore, is measured as a function of time. In this device, as the various individual nucleotide bases pass through the detection window they continuously block and unblock it causing 'events' which give rise to characteristic fluctuations in current flow or resistivity. These fluctuations are then used to generate a suitable data stream for analysis as described above.

The generation of stable droplet streams, especially microdroplet streams, is another developing area of technology that already has applications in molecular biology. For example, U.S. Pat. No. 7,708,949 discloses a novel microfluidic method for generating stable water droplets in oil whilst for example US2011/0250597 describes utilisation of this technology to generate microdroplets containing a nucleic acid template (typically a polynucleotide DNA or RNA fragment) and a plurality of primer pairs that enable the template to be amplified using the polymerase chain reaction. Other patent applications relating to the field generally include JP2004/290977, JP2004/351417, US2012/0122714, US2011/0000560, US2010/01376163, US2010/0022414 and US2008/0003142.

U.S. Pat. No. 6,277,334 describes an apparatus wherein first and second droplets are introduced into reaction wells after passing through a porous reaction support provided with reaction sites where reaction between nucleotides contained in the first and second droplets can be caused to occur. However no mention is made of generating a stream of the droplets from a droplet fluid and an ordered stream of single nucleotides derived from a precursor polynucleotide analyte.

US 2004/0197817 is concerned with an apparatus for fabricating an array of polynucleotides on a substrate by depositing droplets containing the polynucleotide onto a substrate. This apparatus is likewise not directed towards printing a stream of droplets comprising the droplet fluid and an ordered stream of single nucleotides derived from a precursor polynucleotide analyte for the purpose of storing sequencing information.

US 2010/0015614 describes an apparatus for chip-based sorting, amplification and characterisation of biological material using microdroplet polymerase chain reaction amplification followed by capillary electrophoresis analysis. The apparatus includes a planar substrate comprising one or more micro-reactors which are filled using microdroplets containing for example a lysate derived from a cell of a bacterium or virus. However, generating a stream of the droplets from the droplet fluid and an ordered stream of single nucleotides derived from a precursor polynucleotide analyte is not taught EP 1933138 relates to a method for producing a biological assay substrate array by depositing thereon a plurality of conventional biological probes (oligonucleotides and the like) using a droplet printing method. Once again, there is no teaching of generating a stream of the droplets from the droplet fluid and an ordered stream of single nucleotides derived from a precursor polynucleotide analyte.

Recently in our previous applications GB1217772.1, GB1306444.9 and GB1306445.6 we have described a new sequencing method which involves progressive pyrophosphorolysis or exonucleolysis of a polynucleotide to generate an ordered stream of nucleotides which can be captured one-by-one into a corresponding stream of microdroplets. Thereafter each droplet can be chemically and/or enzymatically manipulated to reveal the particular nucleotide it originally contained. However, the analysis of the many millions of droplets potentially generated by such a method frequently requires the droplets to be stored for a period of time whilst the various chemical and/or biological reactions occurring therein proceed to completion. Previously, for storage purposes, we have disclosed a chamber, through which the droplet stream flows, which is adapted to capture and hold the droplets in strict order. However, whilst such a chamber is suitable when the polynucleotide being analysed is relatively short, its use becomes problematic when applied to longer polynucleotides because the large number of droplets quickly leads to an undesirable build-up of back pressure in the chamber which in turns restricts the flow of the microdroplet stream.

We have therefore developed an alternative method which in effect involves storing the droplets at discrete locations on the surface of a substrate where they can be held until they are ready for analysis. Thus, according to the present invention, there is provided a method of storing a stream of droplets, at least some of which comprise one or more single nucleotides and/or oligonucleotides and a droplet fluid, characterised by the step of introducing each droplet sequentially onto a surface of a substrate at a corresponding unique location and further characterised in that the stream of droplets is prepared by a process which includes the steps of generating an ordered stream of nucleotides from the analyte by progressive pyrophosphorolysis or exonucleolysis and capturing each nucleotide in a corresponding droplet.

The substrate upon which the droplets are stored can in principle be made of any inert material including glass, polymers, composites and metals. In one embodiment, the substrate is transparent to electromagnetic radiation especially at the frequencies of visible or near ultra-violet light, for example glass or a transparent plastic. In another it is able to reflect such electromagnetic radiation. In yet another embodiment the substrate is a sheet having an operative surface which is juxtaposed below a droplet delivery system. In this embodiment the surface immediately below the droplet delivery system can either be flat and un-profiled or provided with structures such as grooves, channels, wells, pimples, dimples, holes, pillars and other protuberances which are adapted or shaped to facilitate holding of the droplets. In one example of this, the structures comprise a plurality of wells, grooves or channels in the operative surface typically arranged as a uniform array. These wells, grooves or channels can be any shape as long as they are large enough to at least partially accommodate the droplets and render them immobile in a direction parallel to the operative surface. In one embodiment the wells are substantially hemispherical and have their internal surfaces coated with a light-reflective material.

In another preferred embodiment, parts of the operative surface of the substrate are chemically or physically treated to improve the adherence of the droplets thereto. In one example, this can be achieved by rendering parts of the surface hydrophilic or relatively more hydrophilic than the rest; for example, where the substrate is a glass sheet, by plasma treating or etching the surface to generate surface hydroxyl or hydroxide ion groups at the locations where the droplets are to be delivered. In another embodiment, parts of the operative surface are treated to render them hydrophobic or relatively more hydrophobic than other parts. Thus, the operative surface may comprise a pattern or array of hydrophilic regions on an otherwise hydrophobic surface. In such cases, the hydrophilic or relatively more hydrophilic parts may correspond to some or all of the surface structures mentioned above.

In another example, parts of the operative surface are chemically functionalised or provided with a hydrophilic polymer coating which makes them sticky. In this embodiment, the coating is suitably either transparent to or reflective of electromagnetic radiation of the types mentioned above. In another preferred embodiment, the operative surface is provided with structures of the type mentioned above and at least some of these structures are selectively chemically or physically treated to improve droplet adherence at these target locations only.

When applied to the operative surface, and to a certain extent whilst being applied thereto, the droplets have a tendency to evaporate. This is especially problematic when microdroplets are employed because their evaporative surface area to internal volume ratio is relatively high. Thus, whilst the droplets can be applied directly to an uncoated operative surface of the substrate, it will in certain circumstances be preferred that the operative surface is coated with a film of a liquid which is essentially non-volatile at ambient temperature. Suitably, the thickness of this film should be greater than the diameter of the droplet so that in its stored end-state the droplet is totally encapsulated by the liquid. To facilitate this, it is preferred that the liquid is less dense than the droplet fluid and has a viscosity low enough for the droplet to pass rapidly through the film onto the surface under the influence of gravity. To preserve the integrity of the droplet, the liquid comprising the film should be substantially or completely immiscible with the droplet fluid. Since the droplet fluid is typically an aqueous medium (e.g. water or aqueous buffer), the liquid is thus preferably one which is hydrophobic; for example a fluorocarbon, hydrocarbon or silicone oil. In another embodiment, the liquid is a monomer or polymer which can be cured to create a solid transparent matrix; for example by exposure to heat, ultra violet or microwave radiation. This embodiment has the advantage that the droplets then become trapped in the matrix rendering them immobile and making the substrate easy to transport, manipulate and store for long periods.

Turning to the droplet delivery system, this is designed or arranged with respect to the operative surface of the substrate so that coalescence of adjacent droplets does not occur to any appreciable extent either in the system itself or on the substrate. In one embodiment, the droplet delivery system includes a nozzle having a bore and exit orifice diameter similar to that of the droplets. In one preferred version of this embodiment, the bore of the nozzle at the exit orifice is other than circular in cross-sectional profile, for example triangular, square, rectangular, the shape of a regular polygon, ellipsoidal or the like, in order to facilitate disengagement of the droplets, suitably microdroplets, from the exit orifice and the liquid feed thereto. By this means it may be possible under certain circumstances to dispense the droplets from the droplet delivery system without the need for a carrier medium of the type described below. In another embodiment, and where the droplets are microdroplets, they are suitably delivered to the exit orifice by a microfluidic pathway such as capillary tubing. The internal surface of this microfluidic pathway is suitably rendered hydrophobic to prevent adherence of the droplets thereto. After emerging from the droplet delivery system, the droplets fall under gravity through the liquid film onto the surface of the substrate at the desired location. To further minimise evaporation, in one embodiment it is preferred that the exit orifice of the droplet delivery system is located as close as possible to the surface of the liquid film without actually touching it. In another embodiment, the exit orifice is submerged under the surface of liquid film and preferably the bore of the nozzle at the exit orifice has a non-circular cross-section as mentioned above.

To enable different droplets to be delivered to different unique locations on the substrate the operative surface and the droplet delivery system are adapted to be moveable relative to one another. To achieve this, either of these two components can be moved relative to the fixed other or both can be rendered moveable. Suitably, it is the substrate which is moveable and the droplet delivery system which is fixed. This relative motion, which occurs in at least one, preferably two, spatial dimensions, should take place in a plane parallel to that of the operative surface. Typically this movement will be effected using known methods such as a moveable platform bearing the substrate or the droplet delivery system controlled by one or more servo motors and a microprocessor. Suitably the microprocessor will additionally have a location sensor and a memory in which the order and location of the droplets can be stored for later retrieval.

The droplets employed in the method of the present are suitably microdroplets i.e. droplets having a diameter of less than 50, preferably less than 20 microns. Their shape will generally be determined by the exact design of the apparatus used and may, at various periods of time, be, for example, spherical, oblate spheroidal or ellipsoidal. At least some of these droplets may contain one or more single nucleotides and/or oligonucleotides. Typically these nucleotides or oligonucleotides will themselves comprise one or more common labels in a detectable state. Suitably the detection property associated with these labels will be fluorescence and will arise from one or more fluorophores attached to the nucleotides or oligonucleotides. Preferably the droplet fluid is an aqueous medium.

The nucleotides and oligonucleotides are suitably generated from a precursor polynucleotide analyte, for example a fragment of naturally-occurring or synthetic DNA or RNA, by a process which includes progressive pyrophosphorolysis or exonucleoytic degradation (exonucleolysis) of the analyte to generate an ordered stream of its constituent single nucleotides. In one embodiment, the ordering of the single nucleotides in the stream corresponds to the sequence of nucleotides in the analyte. In another, where the process involves progressive pyrophosphorolysis of a DNA or RNA analyte, the stream of single nucleotides generated comprises respectively a stream of deoxyribonucleoside triphosphates or ribonucleoside triphosphates. In yet another embodiment, where progressive exonucleolysis of a DNA or RNA analyte has occurred, the stream of single nucleotides comprises respectively either a stream of deoxyribonucleoside monophosphates or a stream of ribonucleoside monophosphates. In each of these cases, pyrophosphorolysis or exonucleolysis can suitably be carried out in a flowing aqueous medium so that the nucleotides liberated are continuously removed from the reaction zone. Thereafter, and in one embodiment, the flowing stream containing the individual nucleotides may be converted into a stream of aqueous droplets suspended in an immiscible carrier medium; each droplet being either empty or containing a single nucleotide. In another embodiment, the whole process is carried out so that the ordering of the single nucleotides in this stream of droplets corresponds to the ordering and therefore the original sequence of these nucleotides in the analyte. Thereafter, each droplet in the stream can be subjected to one or more chemical or biological transformations; for example by introducing the necessary chemicals or enzymes thereinto at various points in the droplet flow. In one embodiment of this process, each droplet is treated to capture the nucleotide it contains with a capture molecule which is multiply labelled with fluorophores. Here, the fluorophores are disposed on the capture molecule so that they are non-detectable when the capture molecule is in an unused state; for example by the additional inclusion of quenchers in close proximity thereto or by mutual fluorophore quenching. Thereafter, when the nucleotide has been captured, the 'used capture molecule' becomes susceptible to enzymatic degradation which liberates a cascade of labelled free nucleotides whose associated fluorescence can then be detected. In another embodiment of the process, each droplet is treated to create labelled amplicons characteristic of the nucleotide it originally contained. In this case, the nucleotide is preferably captured and the resulting used capture molecule is amplified to generate a plurality of corresponding amplicons using, for example, the polymerase chain reaction, recombinase polymerase amplification or rolling circle amplification. Thereafter each of the amplicons can be fluorescently labelled using molecular beacons or the like. Further details about these approaches can be found in our various patent applications listed above, the subject-matter of each of which is incorporated by reference.

In one particular embodiment, which is especially useful when the single nucleotides are deoxyribonucleoside triphosphates, the capture molecule comprises a pair of i- and j-shaped oligonucleotides at least one of which is labelled with fluorophore(s) and optionally quencher(s). In the presence of the single nucleotide these pairs can be assembled into a double-stranded oligonucleotide captured molecule which is likewise labelled. In another embodiment this labelled captured molecule is cleaved at a recognition site using, for example, a restriction endonuclease to yield products which in turn can undergo subsequent exonucleolysis to release a cascade of labelled single nucleotides derived from the captured molecule whose associated fluorescence can thereafter be detected. In one embodiment, it is the i-shaped component of the capture molecule pair which is labelled, in another it is the j-shaped component which is labelled and in yet another both components are labelled. In a final embodiment, the capture molecule comprises one or more of the various systems disclosed in our patent applications PCT/GB2013/052594 (published as WO 2014/053853) and PCT/GB2013/052595 (published as WO 2014/053854) the contents, and in particular the capture molecule structural characteristics, of which are incorporated herein by reference.

The droplets can optionally be suspended in a carrier medium. The carrier medium is suitably one which is immiscible with the droplet fluid and is preferably comprised of the same material as the liquid film or at least they are miscible. In one embodiment the liquid film is formed by the carrier medium discharging through the droplet delivery system at the same time as the droplets themselves. In a further embodiment of this an original carrier medium may be replaced at some point in or upstream of the droplet delivery system with a medium more advantageous when it comes to analysing the droplets; for example a carrier which itself is less susceptible to fluorescence.

In another embodiment, the droplets containing the original single nucleotides from the polynucleotide analyte are first delivered to the operative surface and then treated with the various capture molecules, chemicals and enzymes required to effect the various chemical and biological transformations described above. In this case, the necessary capture molecules, chemicals and enzymes can be added to the delivered droplets by, for example, direct injection thereinto and/or adding further droplets containing these materials onto the already delivered droplets under conditions where coalescence can occur.

Once the substrate has been filled with droplets it can be stored until such time as the contents of the droplets are to be investigated. Where the contents are to be analysed by measuring the fluorescence they emit, this can be done, for example, by irradiating each droplet in turn with a focused source of electromagnetic radiation, e.g. from a laser mounted on a moveable assembly, and thereafter measuring the fluorescence emissions of each at one or more characteristic frequencies using a photon detector. By this means, the photon detector can generate a signal, characteristic of the sequence of the polynucleotide analyte, which can then be fed to a microprocessor or stand-alone PC for computational analysis.

The method of the present invention can be advantageously carried out using a microdroplet storage device characterised by comprising:
- a substrate having an operative surface;
- a means for generating a stream of microdroplets which includes the step of generating an ordered stream of single nucleotides from a polynucleotide analyte by progressive pyrophosphorolysis or exonucleolysis;
- a droplet delivery system comprising a nozzle and exit orifice for delivering a stream of microdroplets, at least some of which contain one or more nucleotides and/or oligonucleotides, onto corresponding unique locations on the operative surface;
- a means for delivering the stream of microdroplets optionally in a carrier medium to an inlet of the droplet delivery system and
- a locating mechanism for moving one or both of the substrate and the droplet delivery system relative to the other in the plane of the operative surface.

Suitably the substrate used in the device of the present invention comprises a flat surface, for example a flat sheet or plate, having an operative surface juxtaposed opposite the exit orifice of the droplet delivery system. Preferably, the substrate, and its operative surface, is designed in accordance with one or more of the embodiments listed above and is suitably mounted on either a fixed or moveable platform. In one embodiment, the operative surface is pre-coated with a liquid film as described above before use. Likewise, the droplet delivery system is designed in accordance with one or more of the embodiments listed above and is mounted on either a fixed or moveable platform. In one embodiment, the platform bearing the substrate is moveable and the platform bearing the droplet delivery system is fixed. In another, the platform bearing the substrate is fixed and the platform bearing the droplet delivery system is moveable. In yet another embodiment both platforms are moveable relative to each other. The platforms themselves may be moveable in one or both of the dimensions defining the plane of the operative surface.

The means for delivering the stream of microdroplets to the droplet delivery system is suitably comprised of one or a network of microfluidic paths directly or indirectly attached to an inlet of the droplet delivery system. Suitably the microfluidic paths are adapted to deliver the microdroplets to the droplet delivery system in the form of a stream of microdroplets dispersed in an immiscible carrier medium of the type described above. In one embodiment, the microfluidic path(s) are comprised of a network of microfluidic tube, pipes or the like connected to a first zone; for example a chamber or microfluidic junction, in which the microdroplets are created by means of a droplet-generating orifice where the droplet fluid (typically aqueous) can be caused to issue into the carrier medium. In another embodiment, and in addition to this first zone, the microfluidic paths may further comprise one or a plurality of secondary zones, e.g. chamber(s), microfluidic junctions or injection points, where any, some or all permutations of the nucleotides, the oligonucleotides, the capture molecule(s) and the various chemicals and enzymes referred to above can be introduced into the microdroplet: for example by direct injection into the droplet fluid or droplet coalescence with one or more secondary microdroplet streams. The microfluidic pathway may be provided with one or more heaters and/or coolers at various points along its length to allow temperature control of the stream of microdroplets. It may also be provided with one or more tertiary zones in which the carrier medium can be exchanged for another. Suitably, the microfluidic pathway is fabricated in plastic and the stream of microdroplets is moved therethrough by means of one or more pumps. The microfluidic pathway may be provided with ancillary microfluidic pathways to enable it to be periodically cleaned by flushing.

The locating mechanism suitably comprises the platform and one or more motors which enable the operative surface of the substrate and exit orifice to be positioned precisely with respect to one another immediately in the plane of the operative surface before a microdroplet is caused to issue from the latter. Suitably the device is provided with means to store the exact location in the plane defining the operative surface at which a given microdroplet is delivered so that each data-point can be retrieved on a subsequent occasion. Suitably the location mechanism is a servo-assisted.

In one embodiment, this device may comprise a housing containing the droplet delivery system and a chamber adapted to receive and eject the substrate. The device may optionally further comprise a means for introducing and ejecting a series of substrates sequentially into and out of the chamber; for example by means of a cartridge and/or carousel arrangement. In another embodiment, the device may also optionally include an analysis unit comprising a source of electromagnetic radiation and a photon detector mounted on a moveable assembly. In yet another, the device may also optionally include a microprocessor linked to one or more of the droplet delivery system, the source of electromagnetic radiation (e.g. a laser) and the photon detector. The droplet delivery system is suitably linked or linkable to a droplet sequencer employing one of the processes described above. In one embodiment the means for generating the microdroplets are carried out on a chip and the products thereof delivered microfluidically to the droplet delivery system for printing onto the substrate.

The method is now illustrated with reference to the following Example in which:

FIG. 1 schematically illustrates a sequencer in which microdroplets each containing a nucleotide are made to undergo reaction with a capture system to generate fluorescently labelled amplicons.

Figure 2:
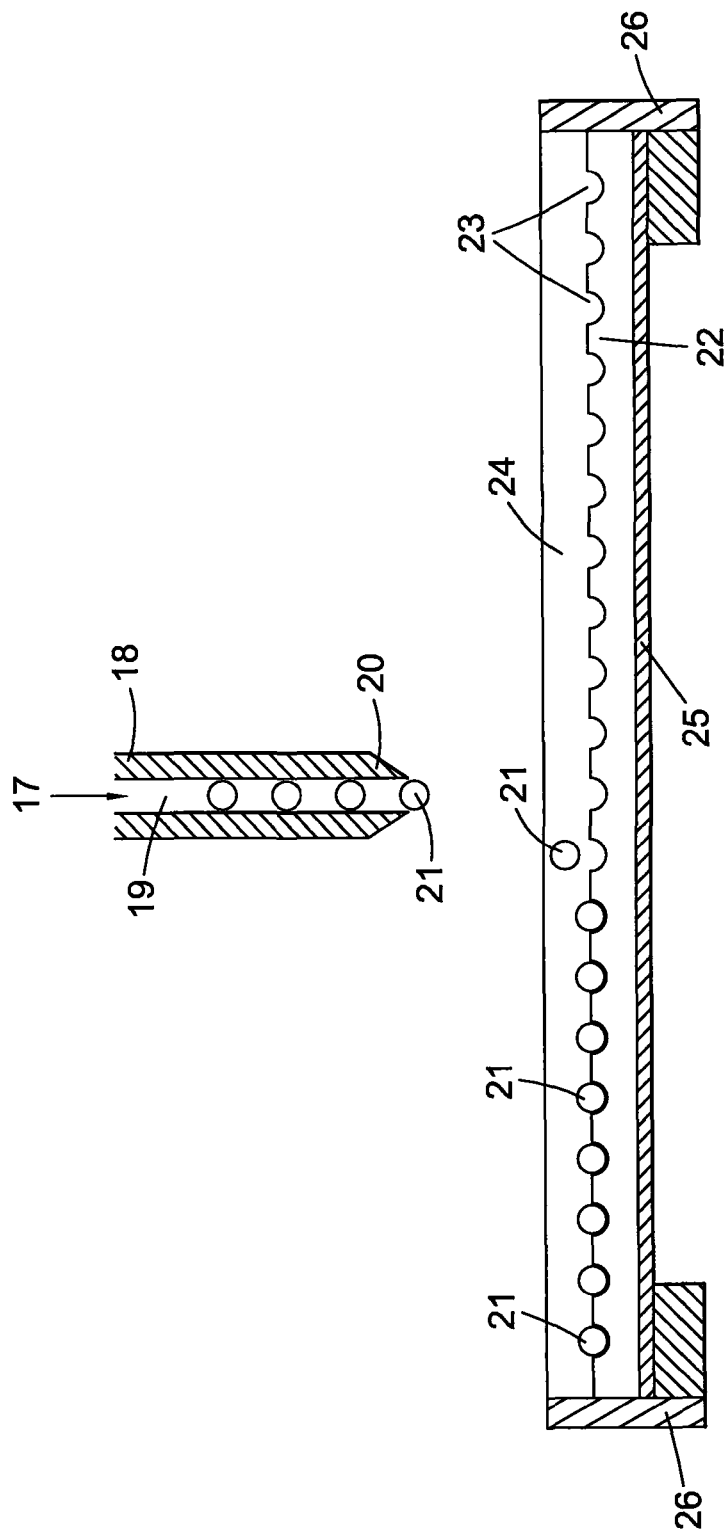

FIG. 2 illustrates a sectional view of a droplet storage device employing the method of the present Invention.

GENERATION OF A STREAM OF MICRODROPLETS EACH CONTAINING OLIGONUCLEOTIDES

An aqueous medium 1 comprising a stream of single nucleotides (deoxyribonucleoside triphosphates) obtained by the progressive pyrophosphorolysis of a 100 nucleotide base polynucleotide analyte derived from human DNA is caused to flow through a ten micron diameter microfluidic tube fabricated from PDMS polymer. The pyrophosphorolysis reaction itself is carried out at by passing a stream of an aqueous, buffered (pH 8) reaction medium at 72° C., comprising Taq Pol and a 2 millimoles per liter concentration of each of sodium pyrophosphate and magnesium chloride, over a glass micro bead onto which the analyte has been previously attached by means of a succinyl bridge. The order of the nucleotides in 1, which is downstream of the micro bead, corresponds to the sequence of the analyte. 1 emerges from a droplet head 2 into a first chamber 3 where it is contacted with one or more streams of immiscible light silicone oil 4. The velocities of these streams are chosen to avoid turbulent mixing and to create aqueous spherical droplets 5 suspended in the oil each having a diameter of approximately eight microns. Typically, rates are adjusted so that between adjacent filled droplets there are on average 10 empty ones. A stream of 5 is then carried forward along a second microfluidic tube of the same diameter at a rate of 1000 droplets per second to a second chamber 6 into which a second stream of five micron aqueous spherical droplets 7 is also fed by means of a second droplet head 8. Droplets 5 and 7 are caused to coalesce in a sequential fashion to form enlarged aqueous droplets 9 approximately nine microns in diameter. Each of 7 contains pyrophosphatase to destroy any residual pyrophosphate anion present in each of 5.

A stream of 9 is then carried forward at the same rate via microfluidic tubing into a third chamber 10 where these droplets are contacted with a third stream of five micron aqueous spherical droplets 11 also fed thereto through a corresponding droplet head 12. The time taken for each of 9 to move between chambers 6 and 10 is c.2 minutes.

Droplets 9 and 11 are then caused to coalesce in 10 to produce droplets 13 (approximately ten microns in diameter). Each of 11 contains a mesophilic ligase and a capture system comprising pairs of four j-shaped first oligonucleotides and four corresponding i-shaped second single-stranded oligonucleotides. Each j-shaped first oligonucleotide is 60 nucleotide bases long and is prepared by folding a 60 nucleotide base single-stranded oligonucleotide precursor about the $45^{th}$ nucleotide base from the 5' end to generate a 3 nucleotide single-stranded loop, a 12 nucleotide base pair double-stranded region and a 33 nucleotide base single-stranded region which is different in each of the four first oligonucleotides. Each of these four first oligonucleotides also has a different $33^{rd}$ base (measured from the single-stranded end) characteristic of the four characteristic nucleotide base types of DNA (i.e. A, T, G and C). The four different i-shaped second oligonucleotides are each 28 nucleotide bases long and have different sequences which are complimentary to that part of the single-stranded region defined by the $4^{th}$ and $32^{nd}$ nucleotide bases of their first oligonucleotide pair.

A stream of 13 is next carried forward at the same rate via microfluidic tubing where after thirty minutes it is passed through a hot spot, where the ligase is caused to deactivate (ten to twenty minutes), before entering into a third chamber 14 where it is caused to coalesce with a fourth stream of five micron aqueous spherical droplets 15 also fed thereto through a droplet head 16. Each of 15 contains four different primer pairs selective for each of the second oligonucleotides, Taq Pol enzyme, the four deoxyribonucleotide triphosphates characteristic of DNA and four different molecular beacons selective for each of the four types of amplicons which can be generated from the four different captured molecules capable of being produced in 13. 15 may also contain other additives typically employed in carrying out the polymerase chain reaction. The stream of the coalesced microdroplets 17 so formed is then subjected to between 20 and 30 thermal cycles of between 60 and 95° C. (c. one cycle per minute) during which time amplification of the unzipped capture molecule occurs by the polymerase chain reaction. At the end of this time 17 is transferred to storage.

Storage of the Microdroplets

17 is introduced into droplet delivery system 18 provided with a silanised capillary bore 19 leading to an exit orifice 20 from which the microdroplets 21 emerge one-by-one. Substrate 22 comprises a glass sheet whose operative surface is patterned with a regular two-dimensional array of hemispherical wells 23. The internal surfaces of 23 are pre-etched by plasma treatment. 22 is coated on its operative surface with a thin film of light silicone oil 24 and on its other surface with a light reflective metal layer 25. 22 is mounted on a platform 26 which is moveable in the plane parallel to its operative surface by means of a microprocessor and servo motors (not shown). In use, each of 21 emerge sequentially from 20 at a unique location established by movement of 26 and fall under gravity through 24 into 23 where they are stored under the oil. When the time comes to analyse the microdroplets, each well is illuminated in turn using a laser and any reflected fluorescence measured by a photodetector connected to a computer (not shown).

The invention claimed is:

1. A method of storing a stream of droplets at least some of which comprise one or more single nucleotides and/or oligonucleotides and a droplet fluid, the method comprising:
   introducing each droplet sequentially onto a surface of a substrate at a corresponding unique location,
   wherein the stream of droplets is prepared by a process comprising generating an ordered stream of nucleotides from an analyte by progressive pyrophosphorolysis and capturing each nucleotide in a corresponding droplet.

2. The method as claimed in claim 1, characterised in that the droplets are introduced onto the surface under conditions which prevent the droplets from coalescing.

3. The method as claimed in claim 2, characterised in that the surface of the substrate is provided with a plurality of wells, grooves, channels, pimples, dimples, holes, pillars or other protuberances to which the droplets are introduced.

4. The method as claimed in claim 1, characterised in that the surface is coated with a film of liquid which is immiscible with the droplet fluid.

5. The method as claimed in claim 4, characterised in that the liquid comprising the film is less dense than the droplet fluid.

6. The method as claimed in claim 4, characterised in that the viscosity of the liquid comprising the film allows the droplets to migrate through the film on to the surface of the substrate.

7. The method as claimed in claim 4, characterised in that the droplet fluid is water or aqueous buffer and the liquid comprising the film is selected from the group consisting of fluorocarbon oils, hydrocarbon oils, silicone oils, and liquid monomers or polymers which can be cured to form a solid transparent matrix by the action of heat or uv radiation.

8. The method as claimed in claim 1, characterised in that at least part of the surface of the substrate is adapted to be relatively more hydrophilic than the rest.

9. The method as claimed in claim 1, characterised in that the droplets are introduced onto the surface of the substrate by means of a droplet delivery system.

10. The method as claimed in claim 9, characterised in that the droplet delivery system includes a nozzle comprising an exit orifice which is other than circular in cross-sectional profile.

11. The method as claimed in claim 9, characterised in that the droplet delivery system and the surface of the substrate are moveable relative to each other in at least one spatial dimension.

12. The method as claimed in claim 11, characterised in that the relative movement of the droplet delivery system and the surface of the substrate is controlled by a microprocessor and a servo-assisted mechanism.

13. The method as claimed in claim 12, characterised in that the microprocessor is provided with memory to store the order and location of each droplet.

14. The method as claimed in claim 9, characterised in that the droplets are delivered to the droplet delivery system in the form of a carrier medium containing a stream of droplets at least some of which contain the nucleotides or oligonucleotides.

15. The method as claimed in claim 14, characterised in that the surface is coated with a film of liquid which is immiscible with the droplet fluid, and the carrier medium and the liquid comprising the film are the same.

16. The method as claimed in claim 1, characterised in that the nucleotides or oligonucleotides contained in the droplets are labelled with one or more fluorophores.

17. The method as claimed in claim 1, characterised in that the stream of droplets has a nucleotide ordering corresponding to that of the sequence of nucleotides in a precursor polynucleotide analyte.

18. The method as claimed in claim 1, further comprising treating each droplet to capture the nucleotide with a capture molecule, wherein the capture molecule is multiply labelled with fluorophores in an inactive state, which after capture is subject to enzymatic degradation.

19. The method as claimed in claim 1, further comprising treating each droplet to create labelled amplicons characteristic of the nucleotide it contains.

20. The method as claimed in claim 19, characterised in that the amplicons are created by a method selected from the group consisting of the polymerase chain reaction, recombinase polymerase amplification and rolling circle amplification.

21. The method as claimed in claim 18, characterised in that (1) at least some of the droplets contain single nucleotides derived from the analyte, and (2) said droplets are delivered to an operative surface of the substrate prior to the additional step in claim 18.

22. A microdroplet storage device comprising:
   a substrate having an operative surface;
   a means for generating a stream of microdroplets which includes the step of generating an ordered stream of single nucleotides from a polynucleotide analyte by progressive pyrophosphorolysis;
   a droplet delivery system comprising a nozzle and exit orifice for delivering the stream of microdroplets, at least some of which comprise -one or more single nucleotides and/or oligonucleotides, onto corresponding unique locations on the operative surface;
   a means for delivering the stream of microdroplets optionally in a carrier medium to an inlet of the droplet delivery system and
   a locating mechanism for moving one or both of the substrate and the droplet delivery system relative to the other in the plane of the operative surface.

23. The microdroplet storage device as claimed in claim 22, characterised in that the means for delivering the stream of microdroplets to the droplet delivery system comprises a microfluidic path.

24. The microdroplet storage device as claimed in claim 23, characterised in that it further comprises a means to store the exact location in the plane defining the operative surface at which a given microdroplet is delivered.

25. The microdroplet storage device as claimed in claim 22, characterised in that the operative surface is pre-coated with a liquid film before use.

26. The microdroplet storage device as claimed in claim 22, comprising a housing containing the droplet delivery system and a chamber adapted to receive and eject the substrate.

* * * * *